United States Patent [19]
Coombs et al.

[11] 3,931,172
[45] Jan. 6, 1976

[54] 1-TERTIARY-BUTYL-3-MORPHOLINO-3-PHENYL-2,1-BENZISOXAXOLINES

[75] Inventors: Robert V. Coombs, Chatham; Goetz E. Hardtmann, Florham Park, both of N.J.

[73] Assignee: Sandoz Inc., E. Hanover, N.J.

[22] Filed: Feb. 25, 1974

[21] Appl. No.: 445,267

[52] U.S. Cl. .................. 260/247.5 EP; 424/248
[51] Int. Cl.² .............................. C07D 263/54
[58] Field of Search ..................... 260/247.5 EP

[56] References Cited
OTHER PUBLICATIONS
Nakagawa et al., Chem. Pharm. Bull. 20(10), 2209–2214 (1972).

*Primary Examiner*—Lorraine A. Weinberger
*Assistant Examiner*—Richard D. Kelly
*Attorney, Agent, or Firm*—Gerald D. Sharkin; Richard E. Vila; Joseph J. Borovian

[57] ABSTRACT

The invention discloses 1-tertiary-butyl-3-morpholino-3-phenyl-2,1-benzisoxazolines having pharmacological activity in animals and useful, for example, as hypolipidemic agents. The compounds may be prepared by reacting a 1-tertiary-butyl-3-phenyl-2,1-benzisoxazolium quaternary salt, e.g., 1-tertiary-butyl-3-phenyl-2,1-benzisoxazolium tetrafluoroborate with morpholine. The 1-tertiary-butyl-3-phenyl-2,1-benzisoxazolium quaternary salt may be prepared by reaction of a corresponding 3-phenyl-2,1-benzisoxazole with tertiary-butanol in the presence of a strong inorganic acid.

6 Claims, No Drawings

1-TERTIARY-BUTYL-3-MORPHOLINO-3-PHENYL-2,1-BENZISOXAXOLINES

The present invention relates to 1-tertary-butyl-3-morpholino-3-phenyl-2,1-benzisoxazoline derivatives, processes for their preparation and their use as hypolipidemic agents. The invention also relates to pharmaceutical compositions and methods for utilizing the pharmacological properties of such compounds.

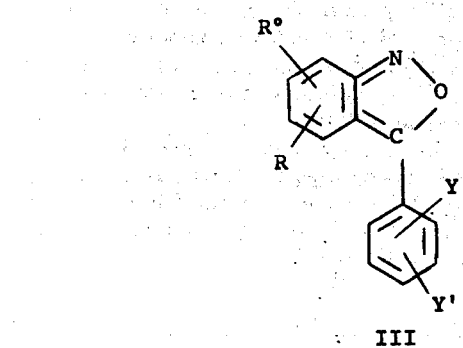

III

The compounds of this invention may be represented by the following structural formula:

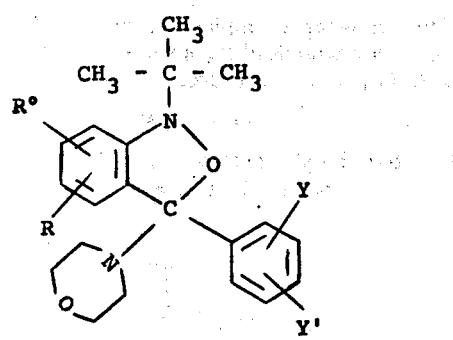

I wherein
R° and R are independently hydrogen, halo of atomic weight of from 18 to 80, lower alkyl of 1 to 4 carbon atoms, lower alkoxy of 1 to 4 carbon atoms or trifluoromethyl, and
Y and Y' are independently hydrogen, halo of atomic weight of from 18 to 80, lower alkyl of 1 to 4 carbon atoms, lower alkoxy of 1 to 4 carbon atoms or trifluoromethyl.

The compounds of formula I may be prepared in accordance with the following reaction scheme:

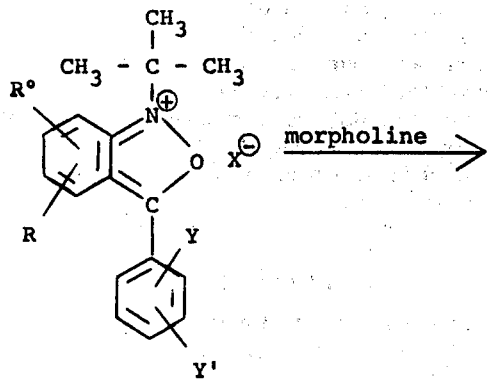

II          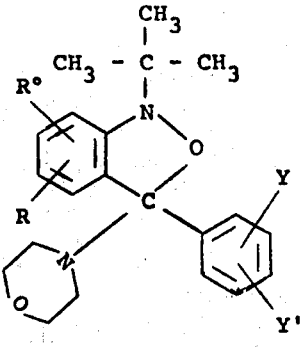    I wherein
R°, R, Y and Y' are as defined above, and
X⁻ is the anion of a strong inorganic acid forming the quaternary salt.

The compounds of formula II may be prepared in accordance with the procedure disclosed in U.S. Pat. No. 3,541,151. Essentially, the procedure involves the following reaction scheme:

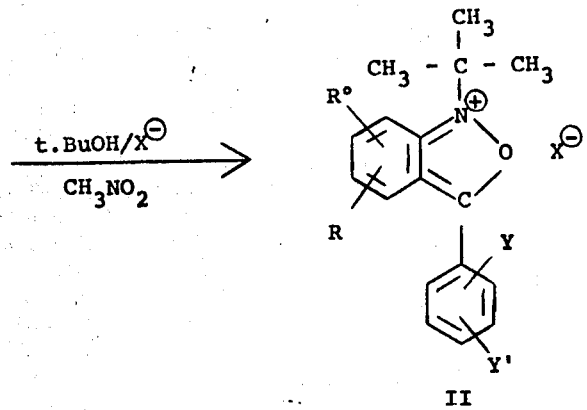

II wherein R°, R, Y, Y' and $X^{\ominus}$ are as defined above.

The preparation of compounds of formula I involves the reaction of a compound of formula II with morpholine. The reaction may be carried out at temperatures in the range of 30°C. to 120°C., preferably between 50°C and 100°C. The reaction product of formula I may be isolated from the reaction mixture by working up by conventional techniques.

The preparation of compounds of formula II may be carried out at temperatures in the range of from 0°C. to 60°C., preferably 10°C. to 35°C., and conveniently at about room temperature. A strong inorganic acid adapted to form a crystalline quaternary salt is required. Acids of this type are known, and include by way of illustration, tetrafluoroboric acid and perchloric acid. The reaction is carried out in the presence of an organic solvent which is inert and adapted to dissolving the reactants and product compound of formula II.

Suitable solvents are known and available, and include by way of illustration, the nitrated hydrocarbons, e.g., nitromethane. The resulting reaction product of formula II may be isolated from the reaction by working up by conventional techniques.

The benzisoxazoles of formula III are either known or can be prepared from known materials by established procedures.

The compounds of structural formula I are useful because they possess pharmacological activity in animals. In particular, the compounds are useful as hypolipidemic agents, particularly hypolipoproteinemia agents, as evidenced, for example, by lowering cholesterol and triglyceride blood serum levels in tests on a group of white rats which are given typically 15 to 250 milligrams per kilogram of body weight per diem of the compound orally, for 6 days, followed by extraction with isopropanol of serum or plasma after anesthetizing the rats with sodium hexobarbital, and then noting the cholesterol and triglyceride contents as compared to those of a control group. The cholesterol and triglyceride contents are determined by the methods described by Lofland, H. B., Anal. Biochem. 9:393 (1964):(Technicon Method N 24a): and G. Kessler and H. Lederer, Technicon Symposium, Mediad Inc., New York, Pages 345–347 (1965), respectively. For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 2 milligrams to about 250 milligrams per kilogram of animal body weight, preferably given orally and in divided doses, 2 to 4 times a day, or in sustained release form. For most mammals, the total daily dosage is from about 140 milligrams to about 1500 milligrams of the compound, and dosage forms suitable for internal administration comprise from about 35 to 750 milligrams of the compound in admixture with a solid or liquid pharmaceutically acceptable carrier or diluent.

For above usage, the compounds of structural formula I may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5 up to about 90 percent of the active ingredient in combination with the carrier or adjuvant, more usually between 3 and 50 percent by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g., calcium carbonate, calcium phosphate, kaolin, peanut oil, sesame oil and corn oil. The preferred pharmaceutical compositions from the standpoint of preparation and ease of administration are solid compositions, particularly hard-filled capsules and tablets.

Capsules containing the ingredients indicated below may be prepared by conventional techniques and are useful in reducing the blood levels of cholesterol and triglycerides in mammals at a dose of one capsule two to four times a day.

| Ingredients | Weight (mg.) |
| --- | --- |
| 1-tertiary-butyl-5-chloro-6-methyl-3-morpholino-3-phenyl-2,1-benzisoxazoline | 150 |
| kaolin | 200 |

The following examples are merely illustrative of specific compounds of the invention and the manner in which they may be prepared.

EXAMPLE 1

1-Tertiary-butyl-5-chloro-6-methyl-3-morpholino-3-phenyl-2,1-benzisoxazoline.

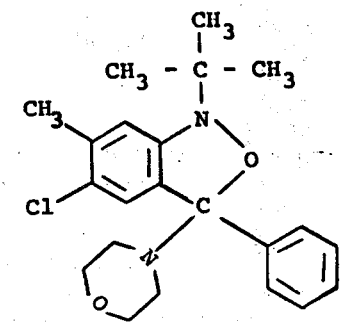

To a flask containing 6 g. of 1-tert.-butyl-5-chloro-6-methyl-3-phenyl-2,1-benzisoxazolium tetrafluoroborate is added 9 ml. of morpholine and the mixture heated at 80°C. for 1 hour. The reaction mixture is washed in diethyl ether and water and the ether layer separated, dried, evaporated in vacuo to dryness and the residue recrystallized from ether/methylene chloride to obtain 1-tert.-butyl-5-chloro-6-methyl-3-morpholino-3-phenyl-2,1-benzisoxazoline, m.p. 131°–133°C.

EXAMPLE 2

1-Tertiary-butyl-5-chloro-3-morpholino-3-phenyl-2,1-benzisoxazoline.

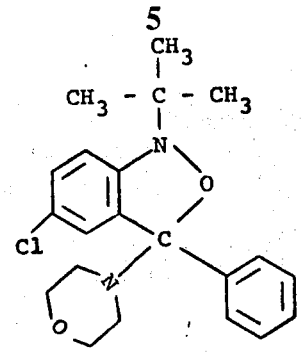

To a flask containing 6 g. of 1-tert.-butyl-5-chloro-3-phenyl-2,1-benzisoxazolium tetrafluoroborate is added 9 ml. of morpholine and the mixture heated at 80°C. with stirring for 1 hour. The reaction mixture is washed in diethyl ether and water and the ether layer separated, dried, evaporated in vacuo to dryness and the residue recrystallized from ether to obtain 1-tert.-butyl-5-chloro-3-morpholino-3-phenyl-2,1-benzisoxazoline, m.p. 130°–132°C.

EXAMPLE 3

Following essentially the procedure of Example 1, and using in place of 1-tert.-butyl-5-chloro-6-methyl-3-phenyl-2,1-benzisoxazolium tetrafluoroborate, an equivalent amount of:

a)   1-tert.-butyl-6-methyl-3-phenyl-2,1-benzisoxazolium tetrafluoroborate,
b)   1-tert.-butyl-5-bromo-6-methyl-3-phenyl-2,1-benzisoxazolium tetrafluoroborate,
c) 1-tert.-butyl-5-bromo-3-phenyl-2,1-benzisoxazolium tetrafluoroborate,
d)   1-tert.-butyl-5-chloro-6-ethyl-3-phenyl-2,1-benzisoxazolium tetrafluoroborate,
e)   1-tert.-butyl-6-ethyl-3-phenyl-2,1-benzisoxazolium tetrafluoroborate,
f)   1-tert.-butyl-5-bromo-6-ethyl-3-phenyl-2,1-benzisoxazolium tetrafluoroborate, there is obtained a)   1-tert.-butyl-6-methyl-3-morpholino-3-phenyl-2,1-benzisoxazoline,
b)   1-tert.-butyl-5-bromo-6-methyl-3-morpholino-3-phenyl-2,1-benzisoxazoline,
c)   1-tert.-butyl-5-bromo-3-morpholino-3-phenyl-2,1-benzisoxazoline,
d)   1-tert.-butyl-5-chloro-6-ethyl-3-morpholino-3-phenyl-2,1-benzisoxazoline,
e)   1-tert.-butyl-6-ethyl-3-morpholino-3-phenyl-2,1-benzisoxazoline,
f)   1-tert.-butyl-5-bromo-6-ethyl-3-morpholino-3-phenyl-2,1-benzisoxazoline, respectively.

EXAMPLE 4

Preparation of
1-tertiary-butyl-5-chloro-6-methyl-3-phenyl-2,1-benzisoxazolium tetrafluoroborate.

To a suspension of 59 g. of 5-chloro-6-methyl-3-phenyl-2,1-benzisoxazole, 26.6 ml. of tert.-butanol and 740 ml. of nitromethane, is added dropwise 45.7 g. of a 50% aqueous solution of tetrafluoroboric acid. The resulting suspension is stirred at room temperature for 85 hours. The reaction mixture is diluted with approximately 10 liters of diethyl ether and the crystalline precipitate formed is isolated by filtration to yield 1-tert.-butyl-5-chloro-6-methyl-3-phenyl-2,1-benzisoxazolium tetrafluoroborate, m.p. 164°–166°C.

What is claimed is:

1. A compound of the formula:

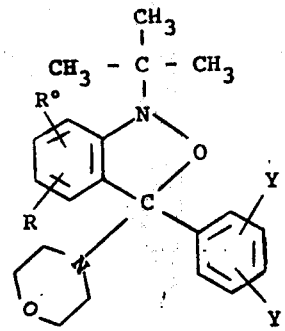

wherein
$R^o$ and R are independently hydrogen, halo of atomic weight of from 18 to 80, lower alkyl of 1 to 4 carbon atoms, lower alkoxy of 1 to 4 carbon atoms or trifluoromethyl, and
Y and Y' are independently hydrogen, halo of atomic weight of from 18 to 80, lower alkyl of 1 to 4 carbon atoms, lower alkoxy of 1 to 4 carbon atoms or trifluoromethyl.

2. A compound of claim 1 having the formula:

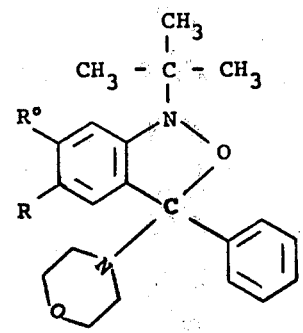

wherein $R^o$ and R are as defined in claim 1.

3. A compound of claim 1 having the formula:

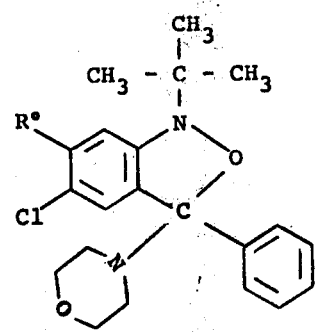

wherein $R^o$ is as defined in claim 1.

4. A compound of claim 1 having the formula:

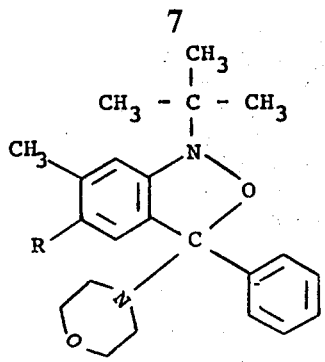
wherein R is as defined in claim 1.
5. The compound of claim 1 which is 1-tertiary-butyl-5-chloro-6-methyl-3-morpholino-3-phenyl-2,1-benzisoxazoline.
6. The compound of claim 1 which is 1-tertiary-butyl-5-chloro-3-morpholino-3-phenyl-2,1-benzisoxazoline.
* * * * *